United States Patent
Chen

(10) Patent No.: US 12,202,813 B2
(45) Date of Patent: Jan. 21, 2025

(54) PROCESS FOR PREPARING 6-(1-ACRYLOYLPIPERIDIN-4-YL)-2-(4-PHENOXYPHENYL)NICOTINAMIDE

(71) Applicant: BEIJING INNOCARE PHARMA TECH CO., LTD., Beijing (CN)

(72) Inventor: Xiangyang Chen, Beijing (CN)

(73) Assignee: Beijing InnoCare Pharma Tech Co., Ltd, Beijing (CN)

( * ) Notice: Subject to any disclaimer, the term of this patent is extended or adjusted under 35 U.S.C. 154(b) by 749 days.

(21) Appl. No.: 17/407,340

(22) Filed: Aug. 20, 2021

(65) Prior Publication Data

US 2021/0380555 A1 Dec. 9, 2021

Related U.S. Application Data

(63) Continuation of application No. PCT/CN2020/076387, filed on Feb. 24, 2020.

(60) Provisional application No. 62/810,305, filed on Feb. 25, 2019.

(51) Int. Cl.
*C07D 401/04* (2006.01)

(52) U.S. Cl.
CPC .................. *C07D 401/04* (2013.01)

(58) Field of Classification Search
CPC . C07D 401/04; C07D 213/81; A61K 31/4545
USPC .......................................................... 546/194
See application file for complete search history.

(56) References Cited

FOREIGN PATENT DOCUMENTS

| CN | 107226805 A | 10/2017 |
|----|-------------|---------|
| WO | 2007117692 A2 | 10/2007 |
| WO | 2015048662 A2 | 4/2015 |

OTHER PUBLICATIONS

Aldrich, Catalogue Handbook of Fine Chemicals, 1999-1998, pp. 1-2 (a cover page & p. 548). (Year: 1998).*
International Search Report for PCT Application No. PCT/CN2020/076387. Mail Date: May 21, 2020. 4 pages.

* cited by examiner

*Primary Examiner* — Taylor V Oh
(74) *Attorney, Agent, or Firm* — Viola Kung; Perkins Coie LLP

(57) ABSTRACT

The present invention relates to processes for preparing 6-(1-Acryloylpiperidin-4-yl)-2-(4-phenoxyphenyl)nicotinamide (Compound I) in a large scale of over 1 Kg. The processes provide a good yield and a purity of at least 95% of the final product and provide a controllable and safe reaction.

5 Claims, No Drawings

PROCESS FOR PREPARING 6-(1-ACRYLOYLPIPERIDIN-4-YL)-2-(4-PHENOXYPHENYL)NICOTINAMIDE

This application is a continuation of PCT/CN2020/076387, filed Feb. 24, 2020; which claims the benefit of U.S. Provisional Application No. 62/810,305, filed Feb. 25, 2019. The contents of the above-identified applications are incorporated herein by reference in their entirety.

FIELD OF THE INVENTION

The present invention relates to processes for preparing 6-(1-acryloylpiperidin-4-yl)-2-(4-phenoxyphenyl)nicotinamide.

BACKGROUND OF THE INVENTION 6-(1-Acryloylpiperidin-4-yl)-2-(4-phenoxyphenyl)nicotinamide (Compound I) is a substituted nicotinamide inhibitor of Bruton's Tyrosine Kinase (BTK). Compound I is useful for treating cancer, inflammation, and autoimmune disease (WO2015/028662). WO2015/028662 discloses a process for preparing about 50 g quantity of Compound I.

There is a need for efficient and purity-controlled processes for preparing Compound I, particularly in a large scale of over 1 Kg.

DETAILED DESCRIPTION OF THE INVENTION

The present invention relates to processes for preparing 6-(1-Acryloylpiperidin-4-yl)-2-(4-phenoxyphenyl)nicotinamide (Compound I) in high purity and good yield. The process is suitable for large-scale production (over 1 Kg, preferably over 2 Kg, over 4 Kg, or over 10 Kg). The process provides purity of Compound I ≥90%, or ≥95%, or ≥98%, or ≥99%.

Compound I

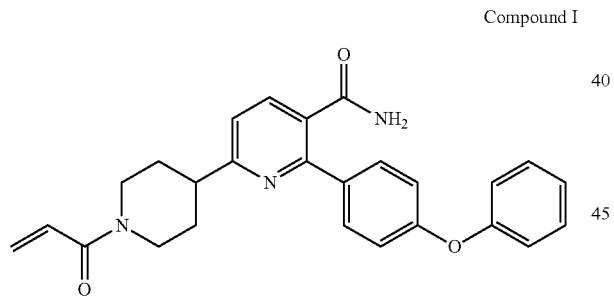

In a first embodiment A, Compound I is prepared from 6-chloro-2-(4-phenoxyphenyl)nicotinamide (INA) and the process uses tert-butyloxycarbonyl (t-Boc) as a protecting group. The process comprises the following steps:

(a) Heating a mixture of INA, SMC, and a first palladium-containing catalyst at 60-140° C. to obtain INB,

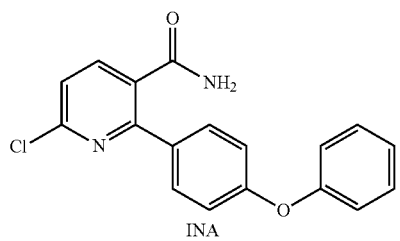

INA

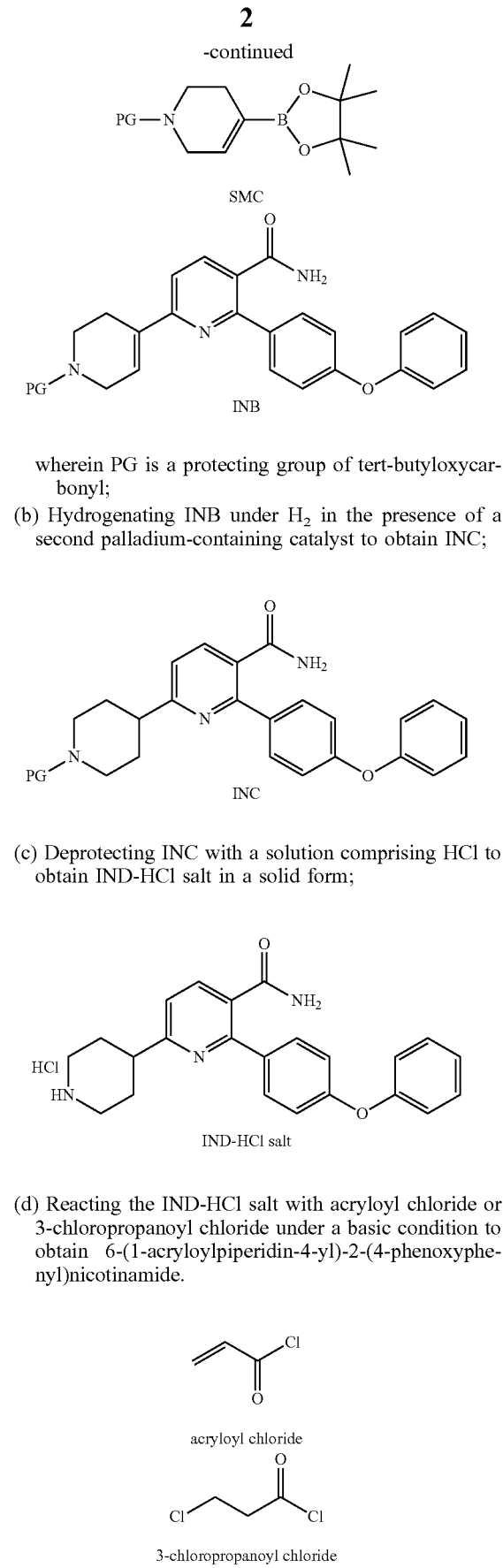

wherein PG is a protecting group of tert-butyloxycarbonyl;

(b) Hydrogenating INB under $H_2$ in the presence of a second palladium-containing catalyst to obtain INC;

(c) Deprotecting INC with a solution comprising HCl to obtain IND-HCl salt in a solid form;

(d) Reacting the IND-HCl salt with acryloyl chloride or 3-chloropropanoyl chloride under a basic condition to obtain 6-(1-acryloylpiperidin-4-yl)-2-(4-phenoxyphenyl)nicotinamide.

acryloyl chloride 3-chloropropanoyl chloride

In step (a), 6-chloro-2-(4-phenoxyphenyl)nicotinamide (INA), tert-butyl 4-(4,4,5,5-tetramethyl-1,3,2-dioxaborolan-2-yl)-3,6-dihydropyridine-1(2H)-carboxylate (SMC), and a suitable palladium-containing catalyst are reacted in a reactor under nitrogen with a low oxygen content (<2%) in a basic aqueous organic solvent mixture to obtain crude tert-butyl 5-carbamoyl-6-(4-phenoxyphenyl)-3',6'-dihydro-[2,4'-bipyridine]-1'(2'H)-carboxylate (INB). The reaction temperature is 60-140° C., preferably 60-100° C., more preferably 75-85° C. The reaction time is typically 1-4 hours. The Pd loading (molar ratio of Pd catalyst over reactant INA) is 0.5-5%. Higher Pd loading speeds up the reaction, but also increases the cost and impurities. Crude INB can be further purified without column chromatography to at least 90% purity by recrystallization and/or trituration, for example, in tetrahydrofuran and ethyl acetate.

Suitable palladium-containing catalysts, as used in this application, include organopalladium compounds such as tris(dibenzylideneacetone)dipalladium(0) ($Pd_2(dba)_3$), tetrakis(triphenylphosphine)palladium(0), bis(triphenylphosphine)palladium(II) dichloride ($Pd(PPh_3)_2Cl_2$), [1,1'-bis(diphenylphosphino)ferrocene]dichloropalladium(II) (Pd(dppf)$Cl_2$), and inorganopalladium compounds, including $Pd(OAc)_2$ with various ligands, for example, $Ph_3P$, $Ph_2Cy$, and $Cy_3P$—$HBF_4$.

In step (b), an organic solution of INB is hydrogenated catalyzed by a suitable palladium-containing catalyst in a reactor under hydrogen to obtain crude tert-butyl 4-(5-carbamoyl-6-(4-phenoxyphenyl)pyridin-2-yl)piperidine-1-carboxylate (INC). The reaction temperature is 15-50° C. and preferably 20-45° C. The reaction time is typically 2-10 hours. The palladium containing catalyst can be Pd/C or $Pd(OH)_2$/C, preferably $Pd(OH)_2$/C which is more process friendly.

In step (c), HCl gas or a solution of HCl is added to an organic solution containing INC and stirred at 10-40° C. for 4-9 hours to remove the protecting group (t-Boc) and to form 2-(4-Phenoxyphenyl)-6-(piperidin-4-yl)nicotinamide (IND)-HCl salt in a solid form. The IND-HCl precipitates from the reaction medium and can be easily collected by filtration or centrifugation, which is suitable for a large scale production. In one embodiment, HCl gas is bubbled into a solution of INC. In another embodiments, an organic solution of HCl (e.g., HCl in ethyl acetate or ethanol) is added to an organic solution of INC (e.g., INC in ethanol or dichloromethane), or the organic solution of INC is added to the organic solution of HCl. The IND-HCl solid can be triturated to at least 90% purity, preferably at least 95% purity, in ethyl acetate.

In step (d), the IND-HCl salt is reacted with acryloyl chloride in a basic solution (pH 8-14, e.g., a bicarbonate solution $HCO_3^-$, a carbonate solution $CO_3^{-2}$, a phosphate solution $PO_4^{-3}$, and a hydroxide solution $OH^-$) at a low temperature (0-8° C. or 2-6° C.) to reduce impurity formation and to obtain Compound I. The solvent of the solution can be an organic solvent (e.g., THF or dichloromethane) with or without water. The reaction time is typically 1-5 hours or 1-3 hours. Alternatively, in step (d), the IND-HCl salt is first reacted with 3-chloropropanoyl chloride in a moderate basic solution (pH 10-12, e.g., a carbonate solution or a phosphate solution) to form an intermediate INE, and then increasing the pH to 14 to a strong basic solution (e.g., a hydroxide solution) to form compound I. The solvent of the solutions can be an organic solvent (e.g., THF or dichloromethane) with or without water.

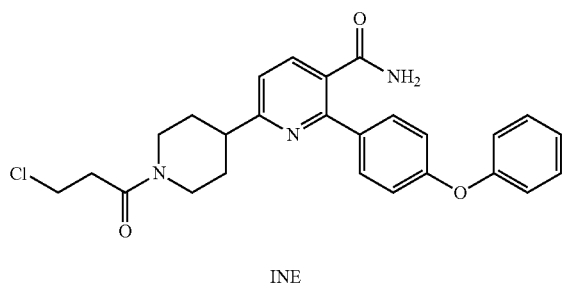 [SMILES: NC(=O)c1ccc(C2CCN(C(=O)CCCl)CC2)nc1-c1ccc(Oc2ccccc2)cc1]

INE

Compound I can be further purified by trituration in THF/water to improve purity to at least 90% purity, preferably at least 95% purity.

In a second embodiment B, Compound I is prepared from 6-chloro-2-(4-phenoxyphenyl)nicotinic acid/ester (INA') and the process uses t-Boc as a protecting group. The process comprises the following steps:

(a) Heating a mixture of INA', SMC, and a first palladium-containing catalyst at 60-140° C. to obtain INB',

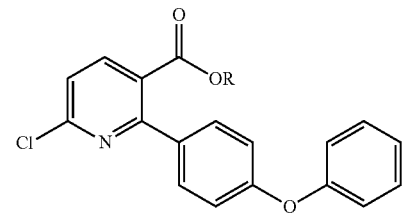

INA'

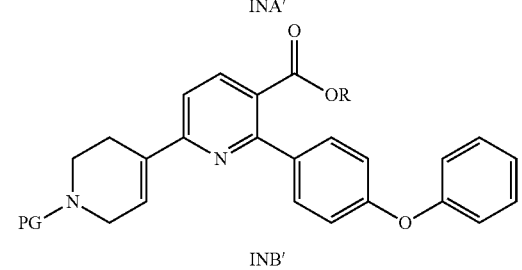

INB' wherein R is H or $C_{1-4}$ alkyl,
PG is a protecting group of tert-butyloxycarbonyl;
(b) Amidating INB' by first treating with oxalyl chloride and then ammonia when R is H, or by reacting with ammonia when R is $C_{1-4}$ alkyl, to obtain INB;

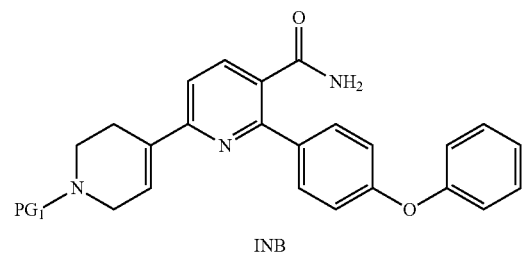

INB (c) Hydrogenating INB under $H_2$ in the presence of a second palladium-containing catalyst to obtain INC;
(d) Deprotecting INC with a solution comprising HCl to obtain IND-HCl salt in a solid form; and (e) Reacting the IND-HCl salt with acryloyl chloride or 3-chloropropanoyl chloride under a basic condition to obtain Compound I.

Embodiment B is similar to Embodiment A except the following. In Embodiment B the starting material is INA' (an acid or ester), not INA (an amide). The product of step (a) is INB' (an acid or ester), which needs to be amidated to INB before hydrogenation. In step (b), when R is H, INB's is first treated with oxalyl chloride in an organic solvent (e.g., THF) at 15-50° C. for 2-10 hours to give an acyl chloride intermediate which is then reacted with 20-35% (w/w) ammonia in water at 15-50° C. for 1-5 hours. In step (b), when R is $C_{1-4}$alkyl, INB' in an organic solution (e.g., THF) is treated with 20-35% ammonia (w/w) in water for at 15-75° C. for 4-20 hours.

In a third embodiment C, Compound I is prepared from 6-chloro-2-(4-phenoxyphenyl)nicotinamide (INA) and uses benzyl or carboxybenzyl as a protecting group. The process comprises the following steps:
(a) Heating a mixture of INA, SMC', and a first palladium-containing catalyst at 60-140° C. to obtain INB, (c) Reacting IND with acryloyl chloride or 3-chloropropanoyl chloride under a basic condition to obtain 6-(1-acryloylpiperidin-4-yl)-2-(4-phenoxyphenyl) nicotinamide.

Embodiment C is similar to Embodiment A except Embodiment C uses a different protecting group of benzyl or carboxybenzyl as a reagent in step (a). Such a protecting group is not stable during hydrogenation, and is deprotected during step (b) to form IND. IND can then react with acryloyl chloride or 3-chloropropanoyl chloride in a basic condition to form Compound I. Optionally, after step (b), a solution comprising HCl can be added to IND to form an IND-HCl salt in a solid form, and then reacting it with acryloyl chloride or 3-chloropropanoyl chloride.

In a forth embodiment D, Compound I is prepared from 6-chloro-2-(4-phenoxyphenyl)nicotinic acid/ester (INA') and uses benzyl or carboxybenzyl as a protecting group. The process comprises the following steps:
(a) Heating a mixture of INA', SMC', and a first palladium-containing catalyst at 60-140° C. to obtain INB',

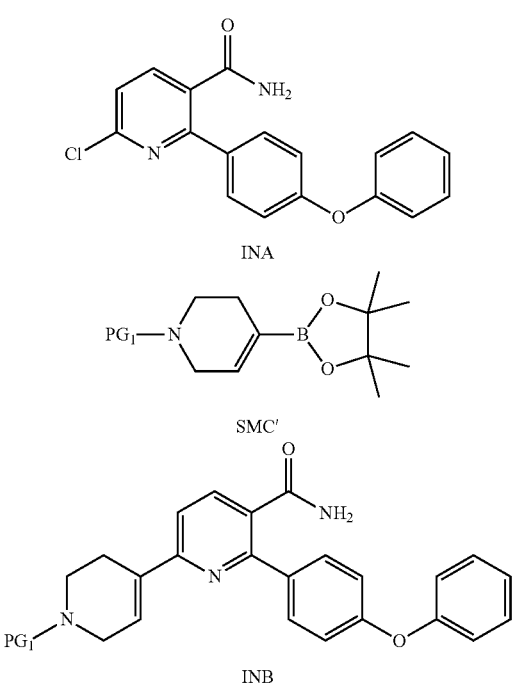

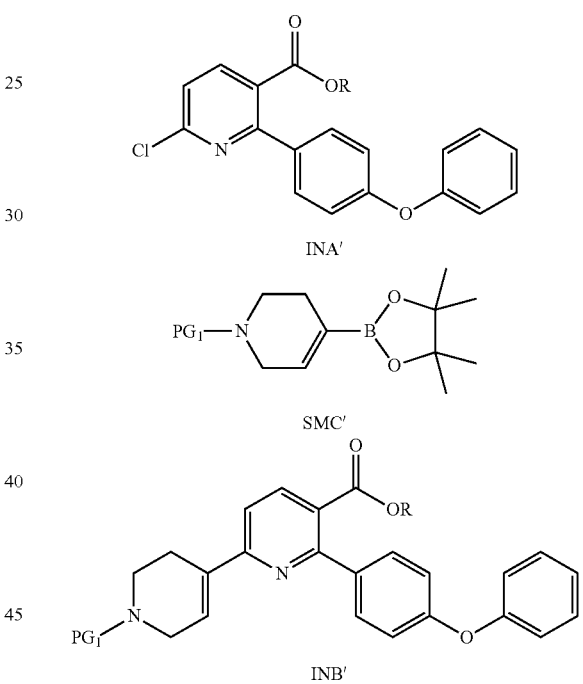

wherein R is H or $C_{1-4}$ alkyl,
$PG_1$ is a protecting group of benzyl or carboxybenzyl;
(b) Amidating INB' by first treated with oxalyl chloride and then ammonia when R is H, or by reacting with ammonia when R is $C_{1-4}$ alkyl, to obtain INB;

wherein $PG_1$ is a protecting group of benzyl or carboxybenzyl;
(b) Hydrogenating INB under $H_2$ in the presence of a second palladium-containing catalyst to obtain IND;

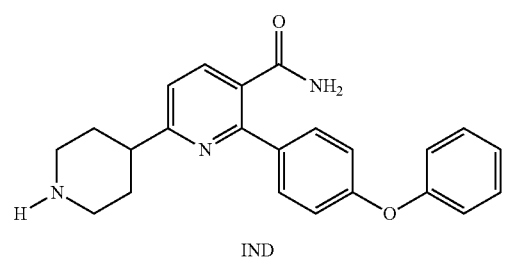 [SMILES: NC(=O)c1ccc(C2CCNCC2)nc1-c1ccc(Oc2ccccc2)cc1 ; "IND"]

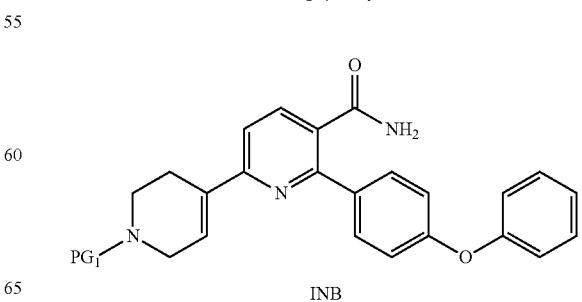

(c) Hydrogenating INB under H$_2$ in the presence of a second palladium-containing catalyst to obtain IND;

(d) Reacting IND with acryloyl chloride or 3-chloropropanoyl chloride under a basic condition to obtain 6-(1-acryloylpiperidin-4-yl)-2-(4-phenoxyphenyl)nicotinamide.

Embodiment D is similar to Embodiment C except the following. In Embodiment D, the starting material is INA' (an acid or ester), not INA (an amide). The product of step (a) is INB' (an acid or ester), which needs to be amidated to INB before hydrogenation. In step (b), when R is H, INB's is first treated with oxalyl chloride in an organic solvent (e.g., THF) at 15-50° C. for 2-10 hours to give an acyl chloride intermediate which is then reacted with 20-35% (w/w) ammonia in water at 15-50° C. for 1-5 hours. In step (b), when R is C$_{1-4}$alkyl, INB' in an organic solution (e.g., THF) is treated with 20-35% ammonia (w/w) in water for at 15-75° C. for 4-20 hours.

The starting material INA can be prepared by heating a mixture of 2,6-dichloronicotinamide (SMA), SMB, and a palladium-containing catalyst in a basic solvent or solvent mixture (e.g., sodium or potassium carbonate, 1,4-dioxane, dimethylacetamide, ethanol/methanol) at 60-140° C. for 8-12 hours to obtain INA.

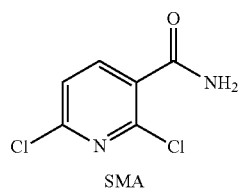

SMA

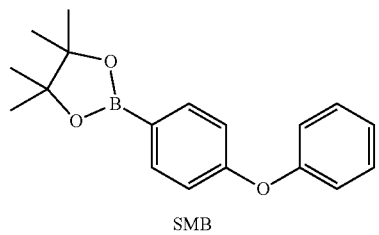

SMB

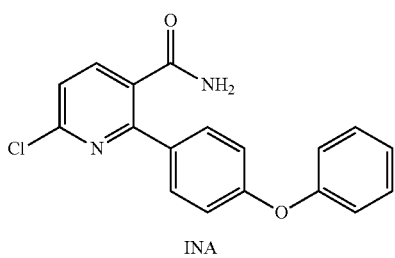

INA

The starting material INA' can be prepared by heating a mixture of 2,6-dichloronicotinic acid/ester (SMA'), SMB, and a palladium-containing catalyst in a basic solvent or solvent mixture (e.g., sodium or potassium carbonate, 1,4-dioxane, dimethylacetamide) at 60-140° C. for 8-12 hours to obtain INA'.

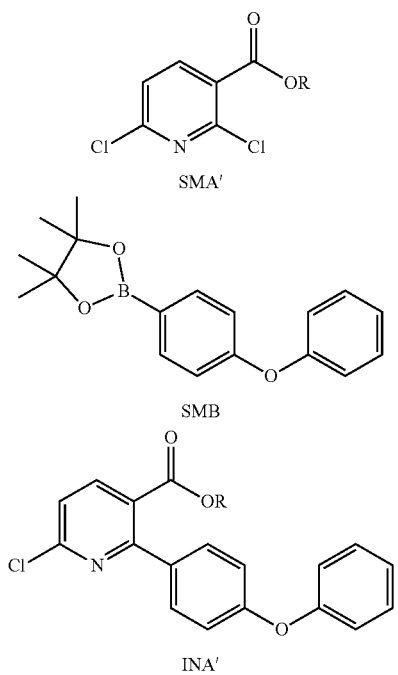

In the process of preparing INA or INA', a boronic ester of SMB is used. SMB works better than the corresponding boronic acid in that SMB reduces di-coupling side reactions and improves regio-selectivity of chloro. The crude INA can be further triturated in tetrahydrofuran to improve purity to at least 90%.

2,6-Dichloronicotinamide (SMA) can be obtained from a commercial supplier. Alternatively, SMA can be prepared by reacting 2,6-dichloronicotinic acid (SM1) with oxalyl chloride (COCl)$_2$ between 10-30° C. for 4-12 hours, followed by reacting with an aqueous ammonia in an organic solvent between 10-30° C. for 1-3 hours.

2,6-Dichloronicotinic acid/ester (SMA') can be obtained from a commercial supplier.

The present process provides a good yield of Compound I. The overall yield from INA or INA' to Compound I is about 55-70%, and from SMA or SMA's to Compound I is about 30-50%.

The following examples further illustrate the present invention. These examples are intended merely to be illustrative of the present invention and are not to be construed as being limiting.

EXAMPLES

Examples 1-6 are summarized in Scheme A.

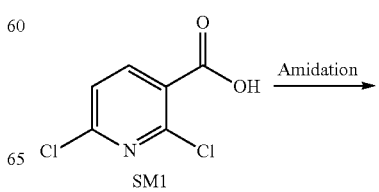

SM1

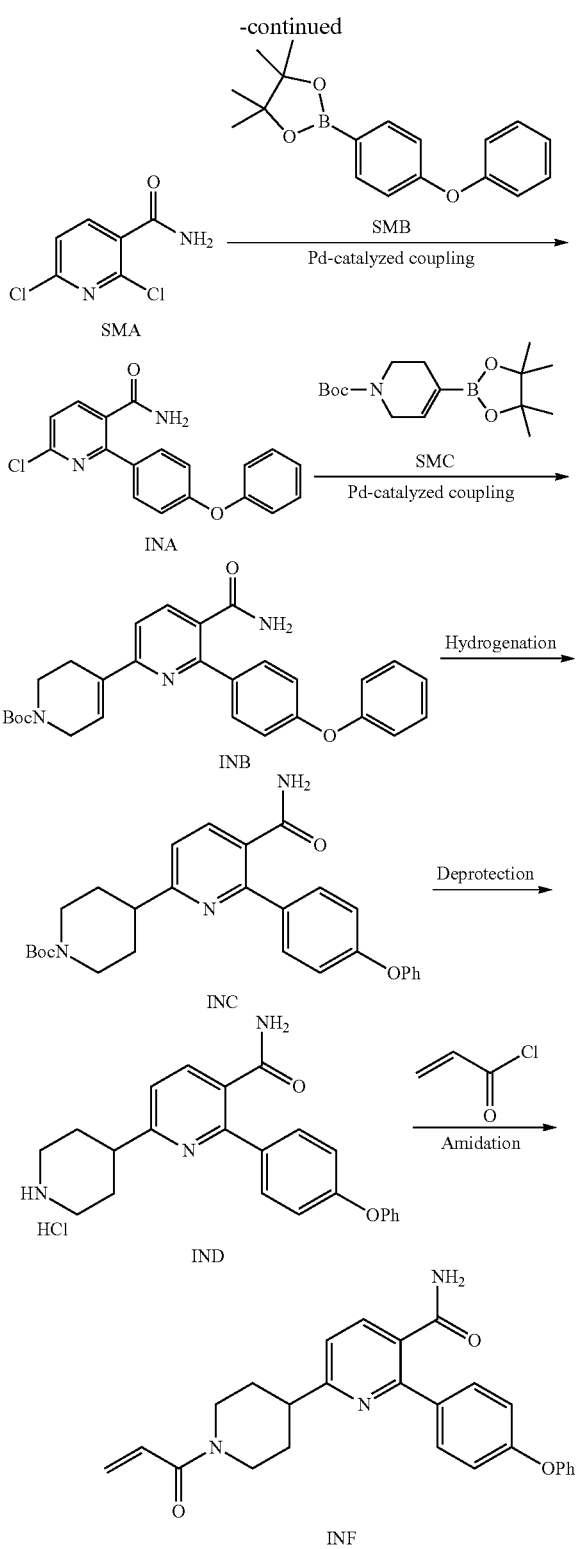

Example 1. Preparing 2,6-dichloronicotinamide (SMA)

A reactor under nitrogen was charged with 2,6-dichloronicotinic acid (SM1, 39.8 kg, 207 mol), DMF (1.9 kg, 26 mol) and THF (189.9 kg). Oxalyl chloride (36.0 kg, 283 mol) was added slowly to the above solution while maintaining the temperature between 15 to 25° C. After addition, the reaction was stirred at the same temperature for 8 h. While keeping the temperature below 50° C., the mixture was concentrated under reduced pressure until the volume was reduced to 2.5~3.5V. Then the mixture was cooled to 20~30° C. and added to a stirred solution of THF (106.1 kg) and aqueous ammonia (180.0 kg) cooled at 0~10° C. After addition, the reaction mixture was warmed to 20~30° C. and stirred for additional 1.5 h. Then the mixture was concentrated under reduced pressure below 50° C. until no distillate came out. The resulting slurry was cooled to 15~25° C., stirred for 2~4 h and centrifuged. The solid cake was washed with water (40.4 kg) and mixed with methyl tert-butyl ether (148.5 kg). The resulting mixture was heated to 45~55° C. and stirred for 3~5 h. Then it was cooled to 20~30° C., stirred for 1~3 h and centrifuged. The solid cake was washed with methyl tert-butyl ether (6.8 kg) and dried for 16 h under reduced pressure (below −0.080 MPa) at 35~45° C. to give SMA (30.48 Kg, 77% yield, 99.6% purity).

Example 2. Preparing 6-chloro-2-(4-phenoxyphenyl)nicotinamide (INA)

To a solution of SMB (58.7 kg, 198.2 mol) in ethanol (120.0 kg) and methanol (36.3 kg) was added SMA (30.0 kg, 157 mol) and $Na_2CO_3$ (66.6 kg, 628 mol) and the resulting mixture was purged with $N_2$ for three times. Then $Pd_2(dba)_3$ (tris(dibenzylideneacetone)dipalladium(0), 4.32 kg, 4.7 mol) was added and $N_2$ was bubbled for 2~5 min. The reaction mixture was heated to 75~85° C. and stirred for 12 h. Then the mixture was cooled to 15~25° C., stirred for 4~6 h and filtered. The filter cake was soaked in ethanol (30.3 kg) for 10~20 min and filtered. The filter cake was dissolved in THF (268.4 kg), heated to 45~55° C. and stirred for 2~4.5 h. The mixture was cooled to 20~30° C. and filtered. The filtrate was collected. The filter cake was soaked in THF (62.4 kg) for 10~20 min and filtered. The filtrate was collected. The filter cake was further soaked in THF (60.3 kg) for 10~20 min and filtered. The filtrate was collected, combined with the above two batches and concentrated under reduced pressure below 50° C. The residue was added with ethanol (60.1 kg) and concentrated under reduced pressure below 50° C. The residue was added with another batch of ethanol (60.4 kg) and concentrated under reduced pressure below 50° C. The residue was added with ethanol (90.1 kg), heated to 75~85° C. and stirred for 1.5~2.5 h. The resulting mixture was cooled to 15~25° C., stirred for 4~6 h and centrifuged. The solid cake was washed with ethanol (30.1 kg) and dried for 16 h under reduced pressure (below −0.080 MPa) at 35~45° C. to give INA (39.23 Kg, 77% yield, 93.1% purity).

Example 3. Preparing tert-Butyl 5-carbamoyl-6-(4-phenoxyphenyl)-3',6'-dihydro-[2,4'-bipyridine]-1'(2'H)-carboxylate (INB)

A reactor under nitrogen was charged with INA (31.7 kg, 90.7 mol, 93.1% purity), tert-butyl 4-(4,4,5,5-tetramethyl-1,3,2-dioxaborolan-2-yl)-3,6-dihydropyridine-1(2H)-carboxylate (30.8 kg, 99.7 mol), $Na_2CO_3$ (25.1 kg, 237 mol), EtOH (118.7 kg) and $H_2O$ (148.2 kg). The reactor was bubbled with $N_2$ until oxygen content was less than 1.0%. Then $Pd(PPh_3)_2Cl_2$ (1.18 kg, 1.68 mol) was added. The reaction mixture was heated to 75~85° C. and stirred for 2.5 h. After cooled to 15~25° C., the reaction mixture was stirred for 1~3 h and filtered. The filter cake was washed with ethanol (26.2 kg) and $H_2O$ (35.8 kg) successively, dissolved in THF (261.7 kg) and stirred at 45~55° C. for 2~4 h. Then the solution was cooled to 20~30° C. and filtered. The filtrate was collected. The filter cake was washed with THF twice (59.3 kg THF and 59.7 kg THF was used respectively) and the filtrate was collected. The three batches of filtrate were combined and concentrated below 60° C. The residue was added with ethyl acetate (148.1 kg) and concentrated below 60° C. Then another batch of ethyl acetate (147.5 kg) was added and the mixture was concentrated below 60° C. The obtained residue was added with ethyl acetate (147.5 kg), heated to 65~75° C. and stirred for 2~4 h. Then the mixture was cooled to 15~25° C., stirred for 2~4 h and centrifuged. The solid cake was washed with ethyl acetate (59.0 kg) and dried for 12~16 h under reduced pressure (below −0.080 MPa) at 35~45° C. to give INB (30.44 kg, 71% yield, 98.7% purity).

Example 4. Preparing tert-Butyl 4-(5-carbamoyl-6-(4-phenoxyphenyl)pyridin-2-yl)piperidine-1-carboxylate (INC)

A reactor under nitrogen was charged with Pd(OH)$_2$/C (2.03 kg, 20%) and THF (32.0 kg) and stirred for 5~10 min. Then a solution of INB (14.85 kg, 31.5 mol) in THF (47 kg) was added. More of THF (32.0 kg) was added and the reaction mixture was purged with N$_2$ for 3 times and then purged with H$_2$ for 3 times while keeping the system temperature between 20 to 25° C. The reaction mixture was heated to 35~45° C. and stirred for 4 h under H$_2$ pressure of 0.10~0.20 MPa. Then the mixture was filtered and the filter cake was washed with THF twice (30 kg×2). The three batches of filtrate were combined to give a solution of crude INC (181.5 kg). Two separate reaction batches (30.5 kg of pure INB was used in total) were combined to give a solution of INC in THF (365.3 kg), which was added with activated carbon (3.00 kg), heated to 45~55° C. and stirred for 1~3 h. Then the mixture was cooled to 20~30° C., filtered with diatomite (15.2 kg) and washed with THF twice (62.2 kg and 61.1 kg of THF was used respectively). The three batches of filtrate were combined and concentrated under reduced pressure below 50° C. The residue was added with ethanol (244.0 kg) and concentrated under reduced pressure below 50° C. More ethanol (246.1 kg) was added and the resulting mixture was concentrated under reduced pressure below 50° C. The residue was added with ethyl acetate (262.3 kg) and ethanol (43.5 kg) and stirred at 20~55° C. until all the solid was dissolved to give the solution of INC.

Example 5. Preparing 2-(4-Phenoxyphenyl)-6-(piperidin-4-yl)nicotinamide (IND)

The above solution of INC in ethyl acetate (262.3 kg) and ethanol (43.5 kg) was purged with N$_2$ for three times. Then HCl (gas, 11.7 kg) was bubbled into the solution and the reaction mixture was stirred at 10~40° C. for 7 h. The mixture was cooled to 15~25° C., stirred for 1~3 h and centrifuged. The solid cake was washed with ethyl acetate (60.8 kg) and dried for 24 h under reduced pressure (below −70 KPa) at 30~50° C. to give IND (26.3 kg, HCl salt, 99% yield, 99.4% purity).

Example 6. Preparing 6-(1-Acryloylpiperidin-4-yl)-2-(4-phenoxyphenyl)nicotinamide (INF)

A reactor under nitrogen was charged with IND (10.0 kg, 24.4 mol), THF (105.5 kg) and H$_2$O (125.4 kg) and the mixture was stirred for 20~40 min at 15~25° C. Then NaHCO$_3$ (10.3 kg, 123 mol) was added in 20~40 min. The reaction mixture was cooled to −2~6° C., added with acryloyl chloride (3.8 kg, 42.0 mol) and stirred for 1~3 h. HPLC showed that IND was not all consumed, so more acryloyl chloride was added and the reaction mixture was continued stirring until completion (0.68 kg of acryloyl chloride was added in three batches and the reaction lasted for 16 h). Then the mixture was warmed to 5~20° C., added with water (98.9 kg), stirred for 20~40 min and filtered. The filter cake was washed with water (20 kg), mixed with another batch of water (100.8 kg) and stirred for 1~2 h at 15~25° C. The mixture was filtered. The filter cake was washed with water (21.2 kg) and ethanol (5.0 kg) successively. Then the filter cake was dissolved in dichloromethane (200.6 kg), heated to 40~45° C. and stirred until the solution became clear. After cooled to 15~25° C., the solution was added with HCl solution (300.7 kg, 0.18%) and stirred for 10~20 min. The two layers were separated. The organic layer was washed successively with water twice (51.0 kg of water and 50.2 kg of water was used respectively), aqueous Na$_2$CO$_3$ solution (0.42%, to adjust pH=8~9) and water (50.0 kg). The organic phase was concentrated under reduced pressure. The residue was added with ethanol (100.0 kg) and concentrated under reduced pressure below 45° C. The residue was further added with ethanol (80.0 kg), stirred for 1~2 h at 15~25° C. and filtered. The filter cake was washed with ethanol and dried for 14 h under reduced pressure at 20~30° C. to give INF (7.47 kg, 72% yield, 99.5% purity).

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude the specification.

What is claimed is:

1. A method for preparing 6-(1-acryloylpiperidin-4-yl)-2-(4-phenoxyphenyl) nicotinamide (Compound I), comprising:

(a) heating a mixture of INA, SMC, and a first palladium-containing catalyst at 60-140° C. to obtain INB,

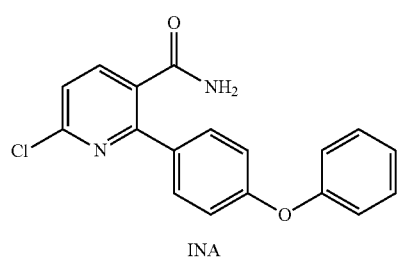

INA

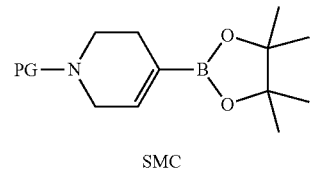

SMC

-continued

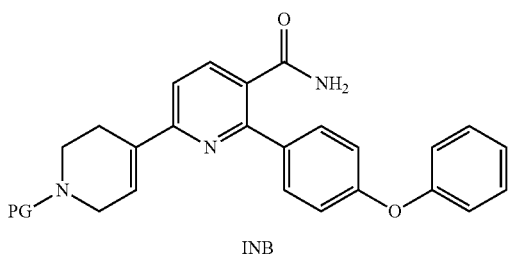
INB wherein PG is a protecting group of tert-butyloxycarbonyl;

(b) hydrogenating INB under H₂ in the presence of a second palladium-containing catalyst to obtain INC;

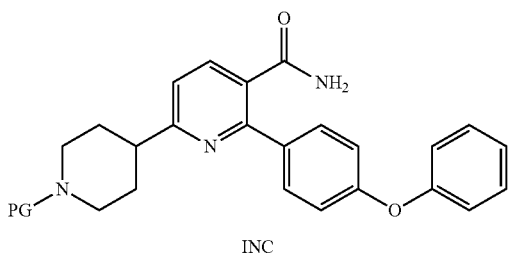
INC (c) adding HCl gas to deprotect INC and obtain IND-HCl salt in a solid form;

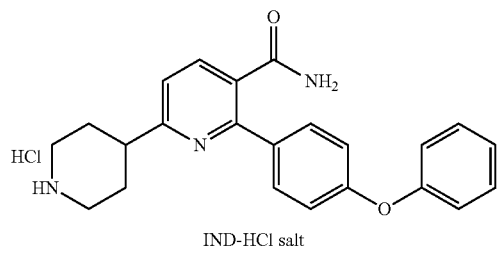 [SMILES: Cl ; NC(=O)c1ccc(C2CCNCC2)nc1-c1ccc(Oc2ccccc2)cc1]
IND-HCl salt (d) reacting the IND-HCl salt with acryloyl chloride or 3-chloropropanoyl chloride under a basic condition to obtain 6-(1-acryloylpiperidin-4-yl)-2-(4-phenoxyphenyl) nicotinamide

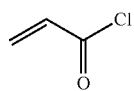
acryloyl chloride

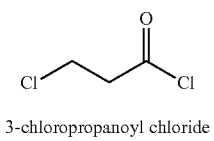
3-chloropropanoyl chloride

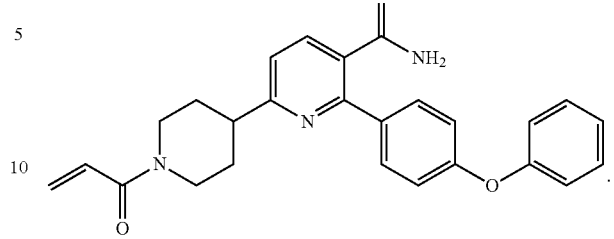
Compound I

2. The method according to claim 1, further comprising a step of heating a mixture of 2,6-dichloronicotinamide (SMA), SMB, and a palladium-containing catalyst in a basic solvent or solvent mixture at 60-140° C. for 8-12 hours to prepare INA

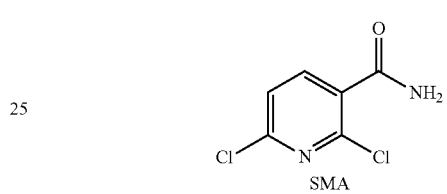
SMA

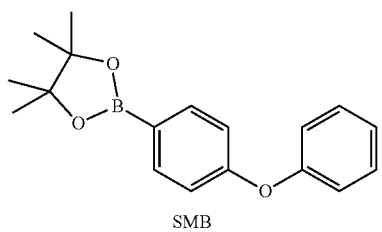
SMB

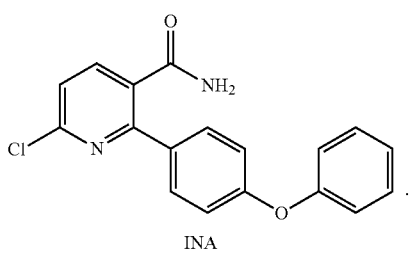
INA

3. The method according to claim 2, further comprising a step of reacting 2,6-dichloronicotinic acid with oxalyl chloride (COCl)₂, followed by reacting with an aqueous ammonia in an organic solvent, to obtain SMA.

4. A method for preparing 6-(1-acryloylpiperidin-4-yl)-2-(4-phenoxyphenyl) nicotinamide (Compound I), comprising:

(a) heating a mixture of INA', SMC, and a first palladium-containing catalyst at 60-140° C. to obtain INB',

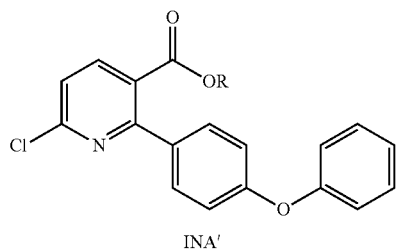

INA'

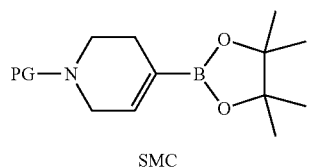

SMC

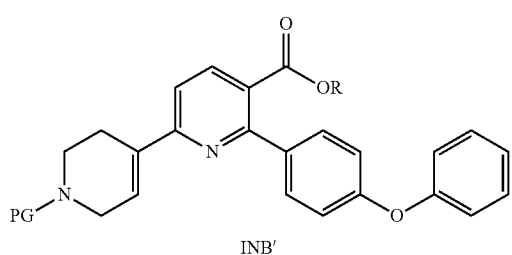

INB' wherein R is H or C_{1-4} alkyl,

PG is a protecting group of tert-butyloxycarbonyl;

(b) amidating INB' by first treating with oxalyl chloride and then ammonia when R is H, or by reacting with ammonia when R is C_{1-4} alkyl, to obtain INB;

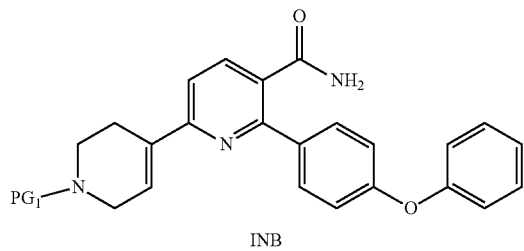

INB (c) hydrogenating INB under H_2 in the presence of a second palladium-containing catalyst to obtain INC;

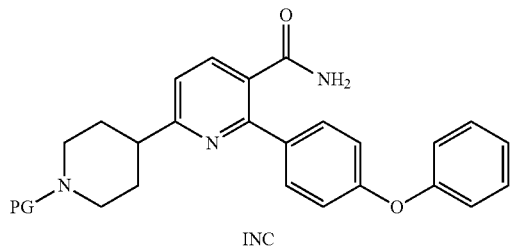

INC (d) adding HCl gas to deprotect INC and obtain IND-HCl salt in a solid form;

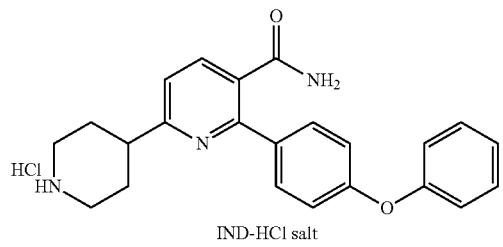 [SMILES: Cl ; NC(=O)c1ccc(C2CCNCC2)nc1-c1ccc(Oc2ccccc2)cc1]

IND-HCl salt (e) reacting the IND-HCl salt with acryloyl chloride or 3-chloropropanoyl chloride under a basic condition to obtain 6-(1-acryloylpiperidin-4-yl)-2-(4-phenoxyphenyl) nicotinamide

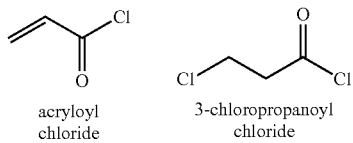

acryloyl chloride 3-chloropropanoyl chloride

Compound I

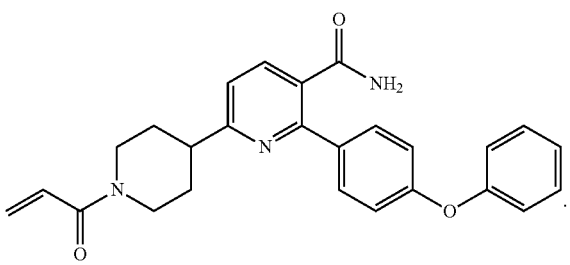

5. The method according to claim 4, further comprising a step of heating a mixture of 2,6-dichloronicotinic acid/ester (SMA'), SMB, and a palladium-containing catalyst in a basic solvent or solvent mixture at 60-140° C. for 8-12 hours to prepare INA'

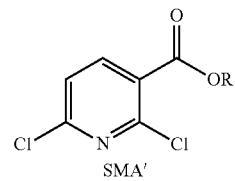

SMA'

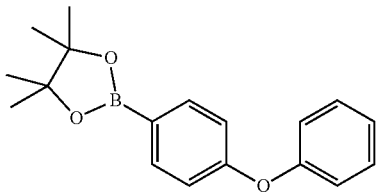

SMB

-continued
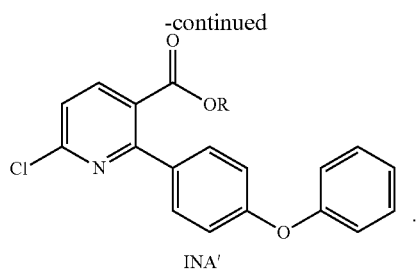
INA'
* * * * *